United States Patent [19]

Liprie

[11] Patent Number: 5,141,487
[45] Date of Patent: Aug. 25, 1992

[54] ATTACHMENT OF RADIOACTIVE SOURCE AND GUIDEWIRE IN A BRANCHY THERAPY SOURCE WIRE

[76] Inventor: Sam F. Liprie, 3409 W. Prien Lake Rd., Lake Charles, La. 70605

[21] Appl. No.: 448,861

[22] Filed: Dec. 12, 1989

Related U.S. Application Data

[63] Continuation-in-part of Ser. No. 61,468, Jun. 15, 1987, which is a continuation-in-part of Ser. No. 897,544, Aug. 18, 1986, abandoned, which is a continuation-in-part of Ser. No. 778,410, Sep. 20, 1985, abandoned.

[51] Int. Cl.⁵ .................................................. A61N 5/00
[52] U.S. Cl. ........................................ 600/7; 128/656; 128/772
[58] Field of Search ................................ 600/1, 3, 6, 7; 128/656–658, 772; 604/282

[56] References Cited

U.S. PATENT DOCUMENTS

| | | | |
|---|---|---|---|
| 2,546,761 | 3/1951 | Loftus | 600/3 |
| 2,559,793 | 7/1951 | Pregal | 600/1 |
| 2,829,636 | 4/1958 | Henschke | 600/1 |
| 3,674,006 | 7/1972 | Holmer | 600/1 |
| 4,244,357 | 1/1981 | Morrison | 600/6 |
| 4,819,618 | 4/1989 | Liprie | 600/3 |
| 4,861,520 | 8/1989 | van't Hooft | 600/7 |
| 4,976,680 | 12/1990 | Hayman et al. | 600/7 |

Primary Examiner—Kyle L. Howell
Assistant Examiner—Robert L. Nasses, Jr.
Attorney, Agent, or Firm—Leitner, Greene & Christensen

[57] ABSTRACT

A source wire for delivery of a radioactive source to the site of a deep body tumor via a relatively narrow passageway includes a relatively thin elongate flexible tube, a solid core running through substantially the entire length of the tube and at least slightly beyond one end of it to strengthen it against collapse while maintaining its flexibility, and a relatively short rigid sleeve overlying the exposed portion of the core and abutting that end of the tube. The sleeve extends at least slightly beyond the otherwise exposed core to accept insertion of the cylindrical filament-like radioactive source to abut against the core. The outer diameter of the sleeve is substantially equal to the outer diameter of the tube and to that of a sheath which overlies the radioactive source and abuts against the end of the sleeve opposite to that abutting the end of the tube. The sleeve is welded to the core and crimped onto the radiactive source for substantially permanent engagement therebetween.

11 Claims, 3 Drawing Sheets

ATTACHMENT OF RADIOACTIVE SOURCE AND GUIDEWIRE IN A BRANCHY THERAPY SOURCE WIRE

This is a continuation-in-part application of co-pending U.S. patent application Ser. No. 07/061,468, filed Jun. 15, 1987; which is a continuation-in-part of U.S. patent application Ser. No. 06/897,544, filed Aug. 18, 1986, now abandoned; which is a continuation-in-part of U.S. patent application Ser. No. 06/778,410, filed Sep. 20, 1985, now abandoned. All of the applications, and U.S. Pat. No. 4,819,618, are hereby incorporated by reference.

BACKGROUND OF THE INVENTION

1. Field of the Invention

The present invention relates to body implants. More particularly, the present invention relates to a method of securing a radioactive filament comprising an iridium/-platinum alloy core and a pure platinum sheath, to a guide member to assure successful maneuvering of the implant through the human body for treatment of body tumors.

2. General Background

In the area of medicine that addresses the treatment of tumors in the body, one such method of treatment is the insertion of implants into the tumor which have been previously radioactive and that emit radioactivity in order to shrink or "kill" a tumor, referred to in the field as Interstitial Brachytherapy.

The procedure involved in this type of therapy would be to insert the radioactive implant through a catheter that has been previously inserted into the tumor from the outside of the body. Once the implant is in the tumor, then the radioactivity emitted by the implant would hopefully destroy the cancerous cells around it. However, there are shortcomings to this technique in utilizing the particular type of implants presently on the market. One of the most common type of implants is the IR-192 (iridium which has been irradiated to render it radioactive) seed implants which are iridium/platinum seeds spaced inside a nylon or plastic tube for insertion into the cancer. The IR-192 seeds are 3 mm in length and are commonly spaced 7 mm apart so that there exists a known standard distance of one (1) centimeter between the centers of the seeds. The IR-192 core contained in each of the seeds cannot be exposed at any of their surfaces to the exterior since the radioactivity would bleed from the iridium core and cause damage. Therefore, it is absolutely necessary that the iridium core be encased in a sheath of platinum at all times. Since there is spacing between the seeds of the nylon or plastic tubing, when inserted into the body of a tumor, the portions of tubing which are not housing the iridium or IR-192 seeds are not emitting radioactivity, and thus the tumor is only being "partially" treated. Likewise, in the cases where the IR-192 seed must be inserted into an area of the body which is not straight, for example an endobronchial implant, tongue implants, tonsil implants, any many other areas that are not readily accessible for treatment, the catheter must be first put in place by traversing a difficult path composed of many turns, tight angles and curves in order to get to the area needing treatment. The IR-192 implant that is to be contained within the catheter can follow only after the tedious task of insertion of the catheters has been accomplished. Since there are spaces between the seeds, many times the nylon or plastic tubing will bend and kink as one attempts to make it move through the curvature of the catheter that leads to the area to be treated, and it becomes impossible to move any further.

Likewise, in addition to the IR-192 seeds, there are some products on the market that are being sold which are pre-determined lengths of encapsulated IR-192 wires. The IR-192 wire implant does have the significant advantage over the IR-192 seed due to the fact that it is a continuous treatment surface and does not contain gaps. However, its shortcomings is that it must be sold only in pre-determined lengths, since any attempt to cut the wire to more precise lengths would cause a leakage in the wire as it would not be self sealing and would thus be unacceptable for use.

Under present guidelines, a radioactive sealed source, whether it is in the form of a wire or seed, has to be leak tested at least every six months. Since the wire is sold in pre-determined lengths and is encapsulated, it is not leaking and is sold as such. Almost every body tumor to be treated is different in size and shape; and, in most cases, more than likely, the wire would have to be cut in order to precisely fit the tumor or cancer area. In the case of IR-192 wire, as was stated earlier, this cannot be done; and therefore, the tumor will not be properly covered.

Further, in order to get the implant (a radioactive part), into the upper lobe for an endobronchial implant, it is necessary that the IR-192 wire be placed into a 0.035" or 0.038" guidewire housing for maneuvering the implant around several curves, etc., within the body in order to reach the upper lobe. In this procedure, the implant is mounted inside a 0.035" or 0.038" guidewire and inserted through a special balloon catheter that is placed through the nasal passage and anchored into place inside the area needing treatment. The problem associated with passing the implant through the balloon catheter is that there is usually one or two sharp angles or curves along this route, especially when inserting into the upper lobe. Previously, in these areas where the curves are difficult, the pressure exerted in attempting to maneuver the implant through the curves would actually cause a kink where the implant and core inside the guidewire meet allowing no further advancement of IR-192 wire implant. The area needing treatment, could not always be reached. Therefore, there is a need to join the iridium wire to the stainless steel wire inside the guidewire, so that no kinking will occur, and the implant can be inserted into the area that needs to be treated.

Further in the area of brain implants, if the IR-192 wire implant would not join to a stainless steel wire of approximately the same outside diameter, the IR-192 wire would have to be mounted inside a small nylon catheter. For example, the nylon catheter presently used has an outer diameter of 0.85 mm. The wire alone is 0.4 mm. A brain implant procedure entails drilling a hole inside the brain for placement of the IR-192 wire. The catheter is slipped inside this hole. If the nylon catheter is used, a hole twice as large than what is needed inside the brain will have to be drilled. By joining the IR-192 wire to a stainless steel wire, one is able to lower it through a hole with the outside diameter smaller than 0.5 mm, since the diameter of the IR-192 wire is only 0.4 mm. Because of the high risk involved in drilling into the brain, the smaller hole is obviously a greater advantage.

U.S. patent application Ser. No. 061,468, entitled "Iridium/Platinum Implant And Method Of Encapsulation", by the same inventor, presently pending, discloses the method by which an IR-192 platinum wire implant, having a core area comprised of 25% iridium and 75% platinum, could be cut to a proper length for use to treat tumors, whereby the method of cutting assured that the end portions of the implant were automatically sealed around the iridium/platinum core so that no radioactive leakage would occur.

U.S. patent application Ser. No. 897,544, entitled "Iridium/Platinum Implant, Method Of Encapsulation, And Method Of Implantation", also by the same inventor, claimed an improvement in the parent application, in that the method of preparing and implanting a radioactive implant into the body included a guidemember that was secured to the implant for guiding the implant to the portion of the body, including a flexible housing for positioning the implant guidemember within the housing. There was applied a compound to the exterior of the housing for achieving a bond between the exterior housing, the implant and guide member, so that the guide member and the implant could be maneuvered to an area of the body and kinking between the implant member and the guide member would be avoided.

Furthermore, U.S. Pat. No. 4,819,618 issued to the samed inventor claims an apparatus and the method for securing a radioactive implant to a guide member to assure successful maneuvering of the implant through a human body which comprises the steps of securing a wire member to the end of a radioactive implant, inserting the implant and the wire member into the guide member to a point so that the junction between the implant and the wire member is surrounded by the guide member, bonding the guide member to the implant of the wire member adjacent the juncture of the implant and the wire member, and arc welding the guide member to the wire member and a plurality of points not adjacent the juncture of the implant and the wire member.

There are several patents which were issued in the field, the most pertinent being as follows:

| Patent No: | Inventor: | Invention: |
| --- | --- | --- |
| 2,429,438 | Wappler | "Tubular Bodies Such As Radium Seeds" |
| 2,322,902 | Wappler | "Apparatus For Making Tubular Bodies" |
| 3,438,365 | Packer, et al | "Radioactive Seed Container Xenon Gas For Medical Treatment" |

SUMMARY OF THE PRESENT INVENTION

The method of the present invention would be an improvement on the methods by the same inventor, including the patent to method under U.S. Pat. No. 4,819,618. The present method would include welding a core member onto a stainless steel tube, pulling the core member until the stainless tube meets an outer housing wound around the core, securing the junction between the housing and the core, along different points between the housing and the core, placing an IR-192 platinum wire inside the stainless steel tube till it meets the core, gluing the wire onto the core, crimping the housing and the IR-192 platinum wire for holding the wire in place, and placing a second tube over the wire to assist in encapsulating the IR-192 platinum wire and also to make the segment of the wire the same outside diameter as the stainless steel tube.

Therefore, it is an object of the present invention to provide the iridium/platinum composite implant to pre-determined lengths for insertion into body tumors;

It is a principal object of the present invention to provide an iridium/platinum composite implant having an iridium/platinum core in a pure platinum sheath;

It is still a further object of the present invention to provide a radioactive implant for body tumors which has a 0.1 mm iridium/platinum core and a 0.15 mm platinum sheath in diameter with a 0.075 mm end thickness of the sheath;

It is still a further object of the present invention to provide a radioactive iridium/platinum composite implant for treatment of body tumors which can be cut and sealed against radioactive leakage simultaneously;

It is still a further object of the present invention to provide a method for cutting pre-determined lengths of iridium/platinum composite of body tumor implant which includes cutting the implant to a pre-determined length and simultaneously sealing the end portions as it is cut, against leakage of radioactivity.

It is a further principal object of the present invention to provide a method for preparing the iridium/platinum composite implant for movement into certain areas of the body; and It is still a further object of the present invention to provide a method for adhering an iridium/platinum composite implant to a stainless steel core wire, comprising the steps of securing a core into a stainless steel tube; providing an outer wire housing around the stainless steel core; securing the junction between the housing and the stainless steel wire and securing the wire around the stainless steel core; placing an IR-192 platinum wire inside the stainless steel tube until joins the end of the stainless steel core; crimping the stainless steel housing and the IR-192 platinum wire with two crimps placed at ninety degree angles from each other to maintain the IR-192 platinum wire in place against the stainless steel core; and providing a nylon tubing the same diameter as the stainless steel tube so as to have a consistent length of wire being inserted into the body.

BRIEF DESCRIPTION OF THE DRAWINGS

For a further understanding of the nature and objects of the present invention, reference should be had to the following detailed description, taken in conjunction with the accompanying drawings, in which like parts are given like reference numerals, and wherein.

DETAILED DESCRIPTION OF THE PREFERRED EMBODIMENT

Figure 1:
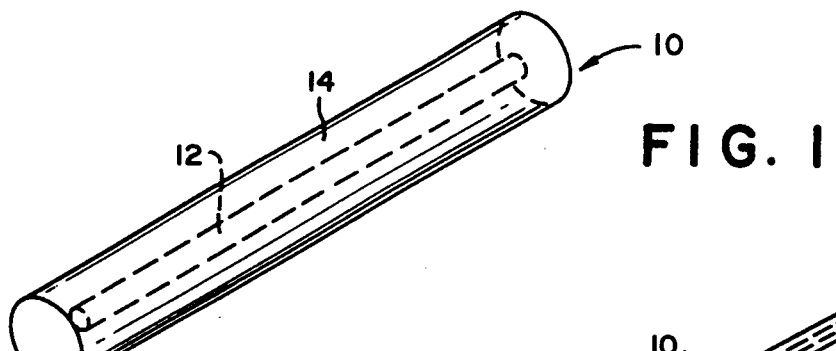
FIG. 1 is an overall perspective view of the preferred embodiment of the implant of the present invention.
Figure 2:
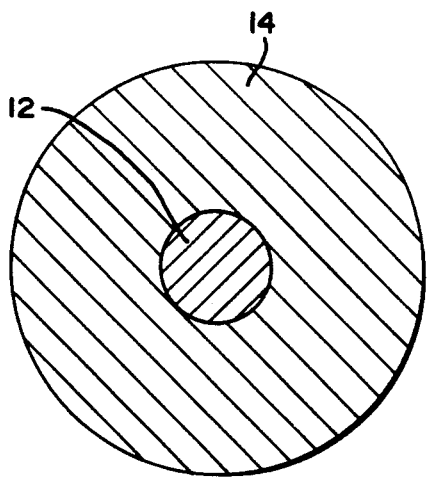
FIG. 2 is a cross sectional view of the preferred embodiment of the implant of the present invention.
Figure 3:
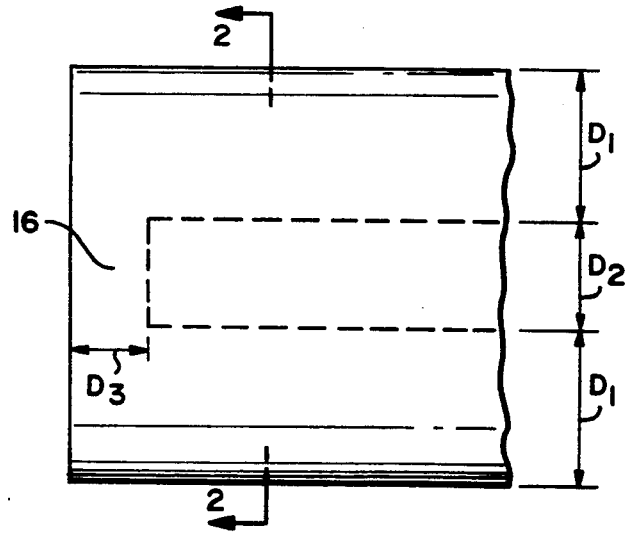
FIG. 3 is a partial side view of the present invention.

FIGS. 1-3 illustrates the initial embodiment of the apparatus of the present invention by the numeral 10, which has been disclosed in applicant's earlier U.S. Pat. No. 4,879,618. Iridium/Platinum composite implant 10 (hereinafter referred to as implant 10), as seen in FIGS. 1 through 3, comprises an inner Iridium/Platinum alloy core member 12 housed in a pure platinum sheath 14. In the preferred embodiment, the Iridium/Platinum core member 12 would comprise 25 percent pure iridium and 75 percent pure platinum in the alloy composite, and would be preferably 0.1 mm in diameter along diameter D2 as seen in FIG. 3. Likewise, pure platinum sheath 14 would comprise 100 percent pure platinum and would have an inside diameter equal to D2, and an outside diameter equal to D1 plus D2 plus D1. Likewise, the preferred embodiment Iridium/Platinum core member 12 would be encased by the pure platinum sheath 14 at its end portions of a thickness of 0.075 mm, as illustrated, indicated as D3 also in FIG. 3.

It is important to note that, at this point, the thickness D1 is crucial in the present invention, as would be illustrated further in the specification, and undertaking the method of cutting the implant 10 to a desired length, the thickness D1 of the pure platinum sheath 14 surrounding the core member 12, that thickness being preferably 0.15 mm, assures the sealing of the end portion 16 as illustrated by thickness D3 also in FIG. 3. This sealing of the end portion is absolutely crucial, since it would prevent any leakage of radioactivity from the cut implant, a problem which now plagues the industry.

Figure 4:
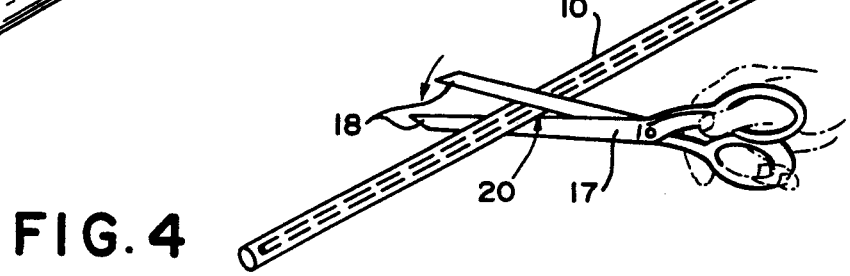
FIG. 4 is an overall view of the method of cutting the implant of the preferred embodiment of the present invention.
Figure 5:
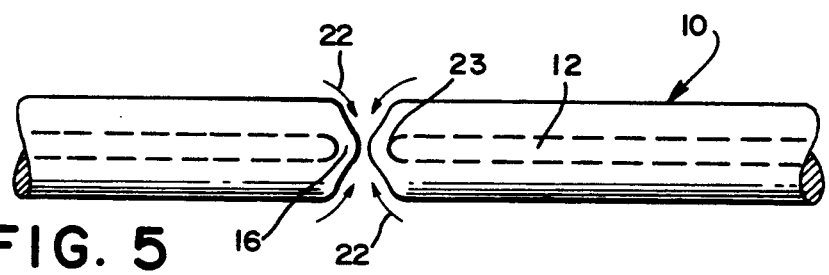
FIG. 5 is a side view illustrating the cut implant of the preferred embodiment of the present invention.

FIGS. 4 and 5 illustrate the method of cutting a length of implant 10, as will be discussed further. The Iridium/Platinum composite implant 10 comprising the iridium core member 12 and platinum sheet 14 could be provided in any length, preferably as a continuous length on a spool or the like. After one has determined a particular length required for a particular body tumor in question, as illustrated in FIG. 4, one would simply utilize preferably a pair of scissors 17 having dulled cutting edges 18 on each blade thereof. Upon determining where along the length of the implant 10 a cut would be made, the scissors would be closed to pinch off the implant wire at point 20. This pinching off the wire at point 20 would, in effect, as seen in FIG. 5, cause the wall of sheath 14 to be squeezed in the direction of ARROWS 22 as seen in FIG. 5, by blades 18, and in effect be squeezed over the cut ends 23 of core member 12 as seen in the FIGURE. FIG. 5 represents the cut ends of the implant 10 following the cutting by scissors 17, with the requisite thickness of 0.075 mm of end portion 16. This, as was stated earlier, ensures that the core member 12 is encased in the platinum sheath along the end portion 16; and therefore, no radioactive leakage would occur.

Again, it should be noted that of particular importance in the design of this inventive implant which allows the dulled scissor blades 18 of scissors 17 to pinch off and seal the ends of the implant 10 in the process, is a factor that the platinum sheath 14 is of the requisite thickness, i.e., 0.15 mm. This particular thickness is great enough to allow and provide for the sealing off of the end portion during the cutting process, yet of the necessary thickness to continue to allow it to be slipped into the plastic catheter 50 for insert.

Therefore, the desirable features of this particular implant and method of cutting to effect the sealing of the end portions now allows this field of medical specialty to provide radioactive implants for body tumors at any desired length needed, following the determination of the shape of the tumor. This is unlike the present state of the art whereby wire must be sold at pre-determined lengths in order to overcome the problem of leakage should the wire be cut. In addition, the present invention allows the implant to be implanted into areas such as were cited earlier wherein a curvature of the implant is required. This particular implant, since it does have a continuous core member, can be bent very effectively and can be implanted into difficult areas which, in the past, have been unable to be effectively treated.

As was stated earlier, a component of the present invention is the fact that an iridium/platinum composite implant is disclosed having an iridium core member 12 and platinum sheath 14, and a certain length of the implant can be achieved without leakage from the iridium core 12 by pinching off the wire at a point at the end of the implant, so that the wall of sheath 14 is squeezed over the ends of core member 12 therefore seal. However, in situations where this implant must be implanted into very difficult areas of the body, for example, the upper lobe of an endobronchial implant process, the implant must be placed within a guidewire moved into the area to be implanted for treatment. However, one of the problems encountered is the fact that as one reaches certain sharp "curves", along the route for getting into the upper lobe, the point of juncture between the iridium/platinum composite implant and the core inside the guidewire, is that a kink occurs at that point, and the implant can proceed no further.

Figure 6:
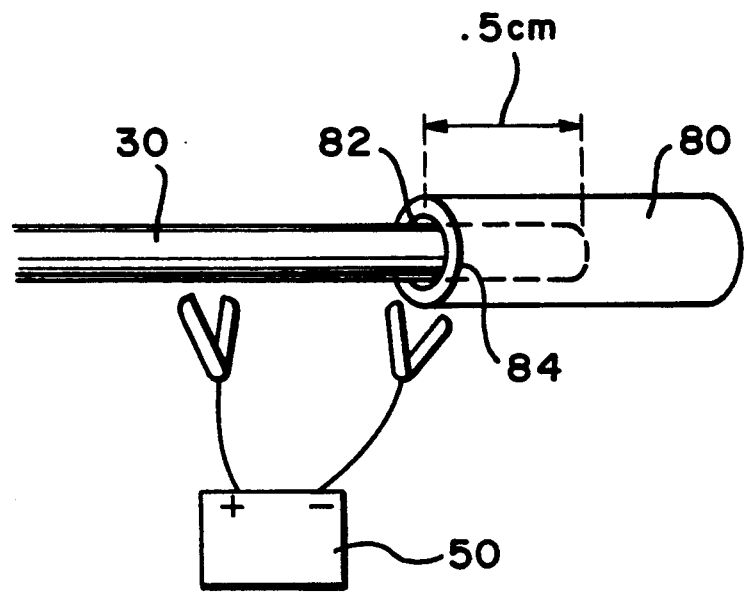
FIG. 6 illustrates a view of the stainless steel core being inserted into the steel tube.

The improved process of the present invention is illustrated in FIGS. 6-10. As illustrated in FIG. 6, stainless steel core member 30 is inserted into a stainless tube 80 which is a sleeve having a length of approximately 1.5 cm, with an inside diameter of 0.5 mm and an outside diameter equal to the outside diameter of the outer housing 34. Core member 30 is then attached to the inner surface 82 of stainless steel tube via welding or the like, at a distance of approximately 0.5 cm within the tube 80. This attachment may be achieved through arc welding via welding unit 50.

Figure 7:
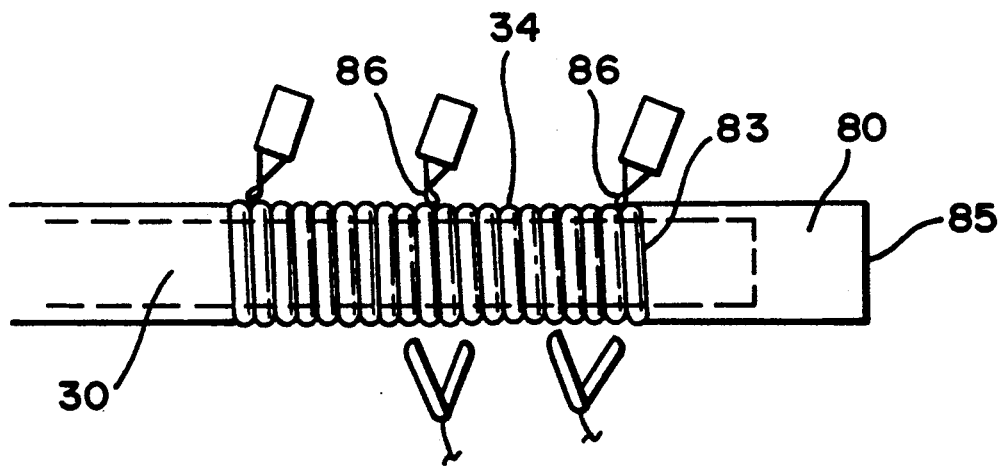
FIG. 7 illustrates a side view of the stainless steel core positioned into the stainless steel tube and further illustrating the outer housing of spring coil wound around the stainless steel core.

After the welding of core 30 into tube 80, outer housing 34, as illustrated in FIG. 7, which actually comprises a tightly wound spring coiled wire around core 30, is maneuvered so that the end portion 83 of outer housing 34 is abutted against the end 84 of stainless steel tube 80. At that point, the end 83 of outer housing 34 is then secured to the end 84 of steel tube 80 via gluing through the use of SUPER GLUE cyanoacrylate ester adhesive bonding material 86 or the like, or a process so that the housing 34 and the stainless steel tube 80 were adhered to one another.

Figure 8:
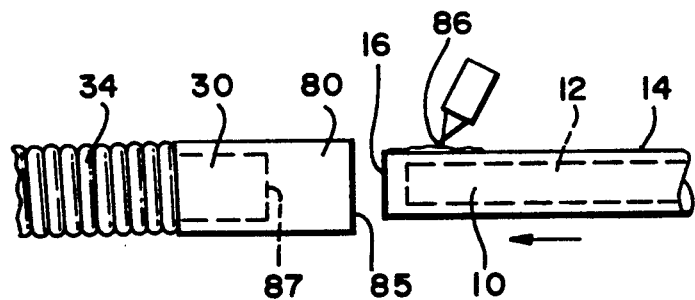
FIG. 8 illustrates the positioning of the IR-192 platinum wire into the stainless steel tube.
Figure 9:
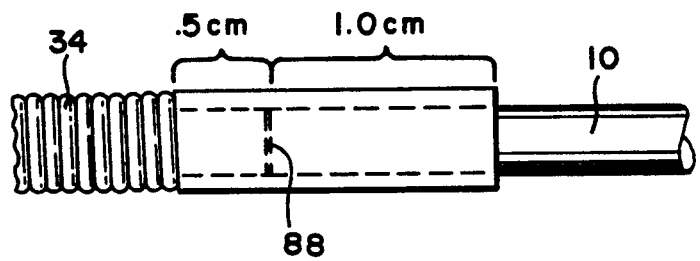
FIG. 9 illustrates the end of the IR-192 wire and the end of the stainless steel core within the tube.

Following that step in the process, FIGS. 8 and 9 illustrate iridium implant 10 being inserted into the second end 85 of stainless steel tube 80 which is substantially the same diameter as core member 30. End 16 of iridium implant 10 is slid into the tube 80, until the end 16 abuts the end 87 of core 30, which is already secured within the bore of tube 80 as was discussed earlier. In order to help secure the implant 10 within stainless steel tube 30, material such as glue 85 or the like is placed on the end of implant 10, so that as end 16 abuts against end 87 of core 30. The end portions are glued in place (as seen in FIG. 9) at point 88, and therefore the implant is, for the time being, held in place.

Figure 10:
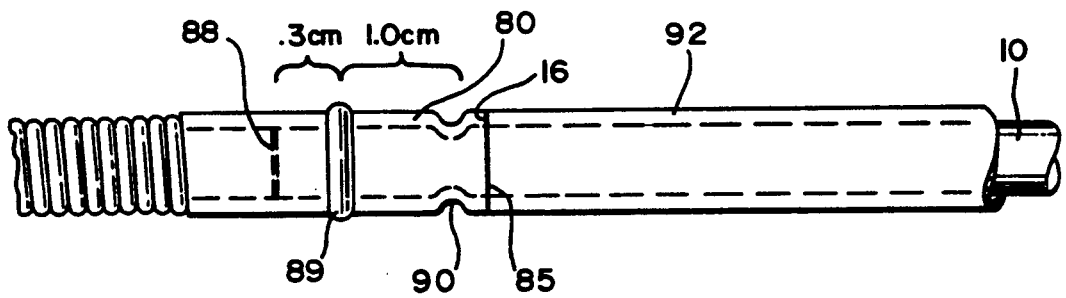
FIG. 10 illustrates the first and second crimps of the stainless steel tube around the end of the IR-192 wire.

Following this step in the process, reference is made to FIG. 10, which illustrates the means for permanently adhering the implant 10 within tube 80. This means would include the process of locating a point substantially 0.3 cm from junction 88 along the length of implant 10, and forming a first crimp 89 in the wall of steel tube 80, to crimp into the surface of iridium implant 10 as seen in FIG. 10. Following that first crimp, a second crimp 90 approximately 1 cm from the first crimp 89 is located along the wall of steel tube 80, and a second crimp is made in the wall of steel tube 80 which again would crimp into the surface of implant 10, as seen in FIG. 10, in order to provide two crimps to maintain the implant in place. In the preferred embodiment, first crimp 89 would be placed at a ninety degree angle from second crimp 90, so that there would be a more uniform adherence between the implant 10 and the steel housing 80 as seen in FIG. 10.

Following the crimping process, a nylon tubing 92 would then be slid over implant 10 (as seen in FIG. 10), the nylon tubing 92 having substantially the same outside diameter as the stainless tube 80 and the outer housing 34, in order to form a uniform diameter wire being inserted into the body. This nylon tubing 92 may be held in place by use of gluing or the like between the wall of the implant 10 and the inner surface of nylon tubing 92.

It should be noted that during the steps of the process, glue may be applied at different points between the connection points between the outer housing 34, the steel tube 80, and the implant 10, so that any voids that might occur during crimping would help to form a very tight seal. The stainless steel tube joint is an advantage in view of the fact that when pressure is applied it will resist breaking, and it will avoid a kink that may occur in the junction.

In practice, the core member 30 and its overlying coil housing or sheath 34 constitute a flexible guidewire by which the implant (the radioactive source) 10 may be handloaded from a point external to the patient's body through a generally narrow, often tortuous passageway such as a natural vessel (e.g., endobronchial passage) or an implanted catheter, depending on the site of the tumor within the body, into position for radiation treatment of the tumor. Accordingly, the core 30/sheath 34 guidewire is of sufficient length to allow the radioactive source to reach the site of the tumor to be treated, and the implant 10 (with overlying sheath 92) is cut to a length (prior to the above-described attachment to the guidewire) appropriate for the size of the tumor under treatment. The source is advanced to the proper location, left in place for the generally brief period prescribed by the oncologist as appropriate for the treatment, and then withdrawn. It will be seen from the foregoing description that the present invention provides a source wire in which the radioactive implant is permanently fastened to the guidewire in a unique manner to allow the source wire to traverse even a very winding passageway without kinking or binding, or the likelihood of separation of the implant from the guidewire.

Because many varying and different embodiments may be made within the scope of the inventive concept herein taught, and because many modifications may be made in the embodiments herein detailed in accordance with the descriptive requirement of the law, it is to be understood that the details herein are to be interpreted as illustrative and not in a limiting sense.

What is claimed as invention is:

1. A source wire for delivery of a radioactive source to the site of a deep body tumor via a relatively narrow passageway, comprising:
   a relatively thin, elongate flexible core member;
   a hollow, rigid tubular member having a length considerably shorter than the length of said core member;
   a thin-walled sheath snugly fastened over said core member to a point exposing a length of the core member shorter than the length of said tubular member, said sheath maintaining the flexibility of said core member and having an outer diameter substantially equal to that of said tubular member and sufficiently small to allow traversal of the sheathed core member through said passageway;
   the exposed length of said core member snugly fastened within one end of said tubular member to a depth at which said one end of the tubular member abuts against the end of said sheath at which the core member is exposed;
   said radioactive source comprising a filament snugly inserted into the end of said tubular member opposite the end into which the core member is inserted and into abutment with the end of said core member within the tubular member;
   said tubular member being crimped over said radioactive source for permanent engagement thereof within the tubular member in abutting relation to the core member; and
   a second thin-walled sheath having an outer diameter substantially equal to that of said tubular member, snugly disposed over said radioactive source and fastened in abutting relation to said opposite end of the tubular member.

2. The invention of claim 1, wherein said tubular member is crimped at least twice over said radioactive source.

3. The invention of claim 2, wherein two of the crimps in said tubular member are spaced-apart in planes along and normal to the length of said tubular member.

4. The invention of claim 3, wherein said two crimps are disposed at substantially right angles to one another about the periphery of said tubular member.

5. A source wire for delivery of a radioactive source to a site requiring radiation treatment within a patient's body, comprising:
   a relatively thin, elongate flexible tube;
   solid core means running through substantially the entire length of the tube and at least slightly beyond one end thereof to strengthen the tube against collapse while maintaining the flexibility thereof;
   a relatively short, rigid sleeve over and extending beyond the portion of said core means exposed at said one end of the tube, said sleeve having an end abutting against said one end of the tube and having an outer diameter substantially equal to the outer diameter of the tube;
   said radioactive source having a substantially cylindrical shape and sized to fit snugly in the sleeve, and inserted into the end of said sleeve opposite that abutting against the tube, in abutment against the end of said core means therein;

said sleeve crimped onto said radioactive source for substantially permanent engagement therewith; and a sheath having an outer diameter substantially equal to the outer diameter of each of the sleeve and the tube, secured over said source with an end of the sheath in abutment with the end of the sleeve into which said radioactive source is inserted.

6. The invention of claim 5, wherein said sleeve is crimped at least twice over said radioactive source.

7. The invention of claim 6, wherein two of the crimps in the sleeve are spaced-apart in planes along and substantially normal to the length of the sleeve.

8. The invention of claim 7, wherein said two crimps are disposed at substantially right angles to one another about the periphery of said sleeve.

9. In a source wire for delivery of a radioactive source to a site requiring radiation treatment within a patient's body via a relatively narrow passageway, in which an elongate guidewire is fastened to the radioactive source to advance and withdraw the source within the passageway, the improvement comprising a relatively short sleeve overlying a portion of each of the guidewire and the source at the juncture therebetween and press fitted onto at least one of them to strengthen the permanence of the fastening between the two.

10. The invention of claim 9, wherein said sleeve is welded to the guidewire and is press fitted to the radioactive source by crimping the sleeve over the source.

11. The invention of claim 10, wherein said sleeve has a plurality of crimps, two of said crimps being made substantially normal to the length of the sleeve and at substantially right angles to one another about the periphery of the sleeve over said radioactive source.

* * * * *